US009589235B2

(12) United States Patent
Ding

(10) Patent No.: US 9,589,235 B2
(45) Date of Patent: Mar. 7, 2017

(54) METHOD FOR MEASURING INDIVIDUAL ENTITIES' INFECTIVITY AND SUSCEPTIBILITY IN CONTAGION

(71) Applicant: Jiali Ding, Beijing (CN)

(72) Inventor: Jiali Ding, Beijing (CN)

( * ) Notice: Subject to any disclaimer, the term of this patent is extended or adjusted under 35 U.S.C. 154(b) by 0 days.

(21) Appl. No.: 14/720,784

(22) Filed: May 23, 2015

(65) Prior Publication Data

US 2015/0339585 A1  Nov. 26, 2015

Related U.S. Application Data

(60) Provisional application No. 62/002,719, filed on May 23, 2014.

(51) Int. Cl.
*G06N 99/00* (2010.01)
*G06N 7/00* (2006.01)
*G06F 19/00* (2011.01)

(52) U.S. Cl.
CPC ......... *G06N 7/005* (2013.01); *G06F 19/3493* (2013.01)

(58) Field of Classification Search
None
See application file for complete search history.

(56) References Cited

PUBLICATIONS

Ding, J. "Modeling Contagion among Customers Using Store Scanner Data." (2009). <retrieved from ckgsb.com>. <retrieved Nov. 18, 2015>.*
Grossman, D., et al. "Learning Bayesian network classifiers by maximizing conditional likelihood." Proceedings of the twenty-first international conference on Machine learning. ACM, 2004.*
Trusov, M. et al. "Determining influential users in internet social networks." Journal of Marketing Research 47.4 (2010): 643-658.*
Dodds, P., et al. "A generalized model of social and biological contagion." Journal of Theoretical Biology 232.4 (2005): 587-604.*
Luo, W., et al. "Identifying infection sources and regions in large networks." Signal Processing, IEEE Transactions on 61.11 (2013): 2850-2865.*
Hartmann, W., et al. "Modeling social interactions: Identification, empirical methods and policy implications." Marketing letters 19.3-4 (2008): 287-304.*

* cited by examiner

*Primary Examiner* — Luis Sitiriche
*Assistant Examiner* — Eric Nilsson
(74) *Attorney, Agent, or Firm* — Dergosits & Noah LLP

(57) ABSTRACT

Measurements of individual-level infectivity, susceptibility and baseline infection risk to biological or social contagion and sensitivity to environmental factors are made for large number of entities from their contact relation, sequential infection occurrences and environmental factors, using computer implemented Markov Chain Monte Carlo and likelihood maximization for Bayesian estimations of an integrated latent trait response model. The method is useful for precise and efficient contagion control and prevention.

21 Claims, 2 Drawing Sheets

|   | A | B | C | D |
|---|---|---|---|---|
| A | 0 | | | |
| B | 1/ 8.9 | 0 | | |
| C | 1/ 4.2 | 1/ 10.9 | 0 | |
| D | 1/ 7.7 | 1/ 8.9 | 1/ 6.3 | 0 |

METHOD FOR MEASURING INDIVIDUAL ENTITIES' INFECTIVITY AND SUSCEPTIBILITY IN CONTAGION

CROSS-REFERENCE TO RELATED APPLICATIONS

This application claims priority from U.S. provisional patent application No. 62/002,719 filed May 23, 2014, which is incorporated herein by reference.

FIELD OF THE INVENTION

This invention relates to techniques for analyzing individual-level contagion dynamics among multilaterally interacted individual entities. More particularly, it relates to statistical and machine learning methods for measuring or inferring individual entities' latent traits for biological and social contagion.

BACKGROUND OF THE INVENTION

Contagion is the spreading of a particular event, such as infectious disease, fashion, product adoption, financial shock, riot or any other contagious events, behaviors and opinions, by one susceptible entity directly or indirectly contacting another infectious entity. For example, like the spreading of infectious disease, fashion contagion happens when someone adopts a style of clothing or a way of behaving of another one. Financial contagion occurs when other institutions are affected by certain financial shocks following some initially affected institutions. It suggests that massive contagion may be driven not only by infectious individuals but also by a critical mass of susceptible individuals (Watts and Dodds 2007), while the former have more impact on the speed of the contagion process, the latter may have more impact on final size" (Goldenberg, Han, Lehmann and Hong 2009). The infectivity and susceptibility of humans, animals or other entities for an infectious disease can be individually heterogeneous, as different hosts might have different worm burden, genes, pathogenicity and immune levels (Keeling and Rohani 2008). For social contagion, individual entities' ability to influence or to be influenced can be variant due to certain personal traits such as being attractive, convincing, charismatic, magnetic, innovative, information-seeking, confident, and assertive, etc (Katz 1957; Weimann 1991; Chaney 2001; Thoburn, 2004; Goldenberg, Han, Lehmann and Hong 2009). Fast measuring and ranking infectivity and susceptibility for biological and social contagion at individual level can help control the contagion process more precisely and efficiently. For example, with infectivity and susceptibility estimates and ranks of each individual entity, one can identify those key individuals who might have the potential of disproportionally affecting the spread of contagion, and thus implement more efficient vaccination and quarantine, or more in-depth and relevant genetic examinations and pathological research, to optimize our use of limited medical or business resources for contagion control and prevention. In recent years, many firms are picking and relying on contagious consumers as natural trendsetters, rather than expensive celebrities or models, to efficiently influence consumers' product adoption.

In epidemiology, infectivity is usually measured at the population level by incidence, which is the probability of occurrence of a given medical condition in a population within a specified period of time, but not the ability of a specific individual to establish an infection. In social fields, questionnaires based on individual's personality are used to measure individuals' ability to infect others, but the self-report methods of questionnaires take what people claim themselves (or others) to be, and may involve high cost as the number of the surveyed people increases. Here arises a problem: how to measure or infer individual-level infectivity and susceptibility to various contagions for large number of entities?

Today, with the advancement of information technology and data mining techniques, more and more individual-level behavioral and relationship data can be collected and analyzed. That could be a promising direction for solving the problem. However, most quantitative works related to contagion have primarily focused on population-scale epidemic rather than individual-level dynamics. Usually these works only test the empirical existence of certain contagion, or describe and simulate the diffusion processes in contagion using aggregate and non-individually heterogeneous parameters such as outbreak thresholds and state transferring probability via artificial agents, but seldom estimate heterogeneous individual-level parameters for real people from real world events. Nowadays, the well-known degree centrality concepts in social network analysis are often used to measure individuals' centrality characteristics via observed or inferred relations among people. But the "centrality" measurements based on the number of connections one have, measure "exposure" rather than "virulence". Although the more connections one has, the more exposure he or she can get. But the final impact is given by the multiplication of exposure with virulence. For the purpose of big impact, a virus of high virulence should be identified and be offered more exposure. At individual level, some work has been done on inferring whether or not an individual entity influences his/her specific friend's certain behavior, but it measures dyad "yes-or-no" relationships between people rather than individual specific traits. Capable of inferring underlying trait and ability, item response theory based latent trait models are used for examinee-test interactions in psychometrics, but they commonly do not include environmental covariates for control. (Birnbaum 1968; Freeman 1979; Case 1991; Hambleton and Swaminathan 1985; Dodds and Watts 2005; Rossi, Allenby and McCulloch 2005; Keeling and Rohani 2008; Hartmann et al. 2008; Trusov et al 2009, Luo et al 2013)

SUMMARY OF THE INVENTION

Several aspects of the present invention provide system and method for measuring individual entities' infectivity and susceptibility in biological and social contagion.

One aspect is to raise a new measurement problem: how to fast measure individual-level infectivity and susceptibility to contagion for large number of entities?

Another aspect of the invention is to provide a framework for quantifying and analyzing the problem. Intuitively, if after contacting with a particular infected individual, most of people, no matter how strong they are, will get infected, we probably could infer that particular individual has high infectivity. Similarly, if many people always followed a particular individual to purchase similar clothing in various situations even when the clothing are expensive, not in promotion and with no brand, we probably could say that particular individual has high infectivity in fashion. The present invention defines individual-level infectivity as the ability of an infected entity to increase a susceptible entity's probability of becoming infected after a direct or indirect contact between them, while disentangling effects due to environments and other factors. Thus, an individual with high susceptibility who contacts with an individual with high infectivity under a favorable environment will have higher infection probability. Rather than measuring infectivity without controlling for susceptibility, or measuring susceptibility without controlling for infectivity, or measuring both of them without controlling for environmental covariates, which could result in inaccurate and partial estimates, the present invention include all these factors into one integrative framework to capture various aspects of individual-level contagion dynamics and their synergism. Particularly, it includes (1) any two potential susceptible and infectious individuals' heterogeneous infectivity and susceptibility, (2) their infection status and contact or link strength, (3) environmental or other observable covariates, and (4) individuals' heterogeneous unobservable baseline infection risk.

Another aspect of the invention is to offer a data-driven solution to the problem: at least both the information on connection relationship and the data of sequential incident are needed, and data on environmental conditions can help too. Essentially, the method iteratively learns individuals' infectivity and susceptibility and other latent traits by relating them to individuals' behavioral interdependence in multilateral interactions across multiple occasions, while controlling for other observable and unobservable factors.

Another aspect of the invention is directed to the operation of the solution. Large number of unknown individual-level parameters makes the problem "over parameterized". It's un-identifiable by standard inference methods such as the maximum likelihood estimation. The present invention offers a Bayesian estimation method for jointly estimating large number of individual-level parameters, including detailed formulas for computer implementation. The method comprises the steps of:
  obtaining (1) the contact relation matrix of a plurality of potentially interacted individual entities in terms of single or multiple diseases, products or behaviors in biological or social contagions, (2) the sequence of infection or adoption occurrences for the single or multiple diseases, products or behaviors of each individual entities, and (3) the conditions of environmental and other observable factors confronted by them during the observation period;
  initializing estimate values for (1) each individual entity's infectivity and susceptibility to contagion, which may involve single or multiple diseases, products or behaviors, (2) each individual entity's baseline infection risk (or adoption likelihood), and (3) each individual entity's sensitivity to environmental factors, and (4) other latent variables;
  assigning prior distributions of individual entities' parameters;
  computing and drawing iteratively from the full conditional distributions of individual entities' parameters and other latent variables, given by the Bayesian estimation for an integrative latent trait response model, and
  updating the estimates of each individual entity's parameters and other latent variables, until convergence.

Additional aspects, features, applications and advantages will become apparent to those skilled in the art from the following detailed description and the accompanying drawings.

DETAILED DESCRIPTION

Figure 1:
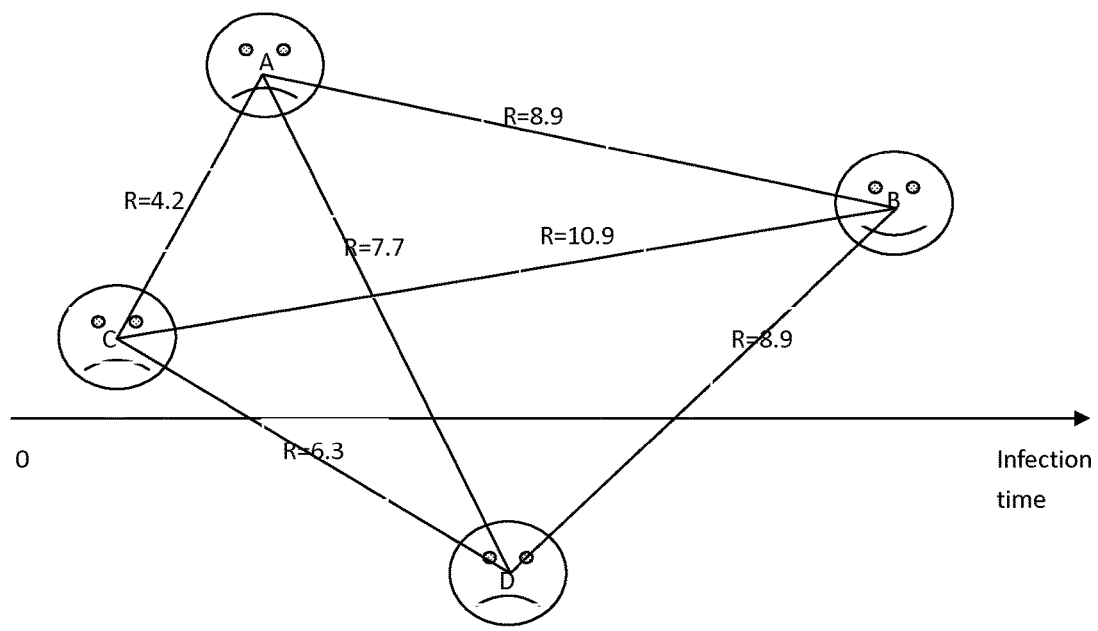
FIG. 1 is a diagram of contact relation matrix among four individual entities' and their sequential infection occurrences.

An interaction network is defined by a set of multilaterally interacted entities and the contact relation among them. A matrix N represents how the individual entities are linked with each other by physical contact in disease contagion or any form of communication in social contagion. If entity i contacts with entity j, the corresponding matrix element $n_{ij}$ is 1, otherwise 0. The elements of the contact matrix can also be decimals or some weighted numbers to reflect the likelihood of contact between any two entities, if the explicit and accurate contact between them is not available. For example, the spatial or temporal proximity of two entities can be used as proxy of their contact likelihood. As shown in the upper part of FIG. 1, the elements of contact relation matrix for four multilaterally interacted individuals A, B, C, and D, are calculated using the inverse distance between every two individuals.

In a contagion, we also observe a sequence of infection occurrences of all the individual entities, i.e., we know their infection status (infected or not infected) and the corresponding time. As shown in the lower part of FIG. 1, during the observation period, individuals C, A, and D sequentially get infected while individual B has not.

Assume there are no two infections that occurring at the exactly same time and any two entities are potentially interacted with some contact likelihood.

The probability of the susceptible entity i infecting disease 1 (or adopting product 1) at occasion t is defined according to the present invention as relating to $$\alpha_i^c \zeta_j x_{jl(t-1)} n_{ijlt} + X_{ilt}' \alpha_i^{-c} + \epsilon_{ijlt}, \quad (1)$$

where $\zeta_j$ is the infectivity of potential infectious entity j, $x_{jl(t-1)}$ is the prior infection status (or adoption behavior) of j on disease (or product) 1 before occasion t, $n_{ijlt}$ is the contact probability between i and j in term of disease (or product) 1 till occasion t, $X_{ilt} = [X_{ilt1}, X_{ilt2}, \ldots, X_{iltk}]'$ is i's confronted environmental factors such as temperature, humidity and wind speed etc. (or marketing mix such as price, promotion) and disease (or product) attributes at occasion t, $\alpha_i^c$ is entity i's susceptibility to contagion and vector $\alpha_i^{-c}$ is i's sensitivity to environmental factors and other attributes. Different with aggregate-level models for infectious disease and product diffusion, which typically neglect individual-level dynamics, the present specification accounts for the contingent nature of contagion upon the intrinsic traits, infection status and contact of hosts, as well as individuals' responses to specific environmental and disease (or product) attributes, and thus allows for jointly inference of both infectivity and susceptibility of individual entities. We notice that the infectivity and susceptibility are allowed to be continuous values, not only "yes-or-no" dichotomy or other discrete classifiers, so that they can be further used for comparison and ranking.

Assuming the error term $\epsilon_{ijlt}$ to follow Logistic distribution or standard normal distribution, the probability of entity i infecting disease (or adopting product) 1 conditional on entity j's potential infectivity and all the other factors is:

$$P(Y_{ijlt} = 1 \mid \zeta_j, \alpha_i^c, \alpha_i^{-c}, x_{jl(t-1)}, n_{ijlt}, X_{ilt}) = \quad (2)$$

$$\Lambda(\alpha_i^c \zeta_j x_{jl(t-1)} n_{ijlt} + X'_{ilt}\alpha_i^{-c}) = \frac{\exp(\alpha_i^c \zeta_j x_{jl(t-1)} n_{ijlt} + X'_{ilt}\alpha_i^{-c})}{1 + \exp(\alpha_i^c \zeta_j x_{jl(t-1)} n_{ijlt} + X'_{ilt}\alpha_i^{-c})}$$

or $$P(Y_{ijlt} = 1 \mid \zeta_j, \alpha_i^c, \alpha_i^{-c}, x_{jl(t-1)}, n_{ijlt}, X_{ilt}) = \quad (3)$$

$$\Phi(\alpha_i^c \zeta_j x_{jl(t-1)} n_{ijlt} + X'_{ilt}\alpha_i^{-c}) = \int_{-\infty}^{\alpha_i^c \zeta_j x_{jl(t-1)} n_{ijlt} + X'_{ilt}\alpha_i^{-c}} \frac{1}{\sqrt{2\pi}} \exp\left(-\frac{z^2}{2}\right) dz$$

where $Y_{ijlt}$ is the incident (or adoption behavior) of entity i as being potentially infected by entity j, such that $Y_{ijlt}=1$ denotes an infected status (or adoption) of the disease (or product) l on occasion t and $Y_{ijlt}=0$ otherwise.

Equation (2) and (3) indicate the probability that entity i will infect disease (or adopt product) l on occasion t based on the effects defined in the Equation (1) with only negligible error. Therefore if the value of Equation (1) is very low, the probability of infection or adoption is near to zero. However, sometimes an individual might get infected without contact with other individuals, for instance, via a secondary host such as insects, and thus bears a baseline infection probability greater than zero. Similarly, in some situations, an individual may have non-negligible preference for certain products, which contributes to positive baseline adoption likelihood. For such situations, Equation (2) and (3) can be enhanced to incorporate an individual specific baseline infection risk (or adoption likelihood). Let $\beta_{il}$ denote the baseline probability of entity i infecting disease (or adopting product) l due to unobservable and non-contagion factors. Then corresponding to the Logistic or standard normal distribution of error term, the probability of entity i infecting a disease (or adopting product) l on occasion t is:

$$P(Y_{ijlt}=1 \mid \zeta_j, \alpha_i^c, \alpha_i^{-c}, \beta_{il}, x_{jl(t-1)}, n_{ijlt}, X_{ilt}) = \beta_{il} + (1-\beta_{il})\Lambda \quad (4)$$
$$(\alpha_i^c \zeta_j x_{jl(t-1)} n_{ijlt} + X'_{ilt}\alpha_i^{-c})$$

or $$P(Y_{ijlt}=1 \mid \zeta_j, \alpha_i^c, \alpha_i^{-c}, \beta_{il}, x_{jl(t-1)}, n_{ijlt}, X_{ilt}) = \beta_{il} + (1-\beta_{il})\Phi \quad (5)$$
$$(\alpha_i^c \zeta_j x_{jl(t-1)} n_{ijlt} + X'_{ilt}\alpha_i^{-c})$$

This enhancement makes the present method more general as we can see that if $\beta_{il}=0$, i.e., entity i has zero baseline infection probability for disease (or product) l due to unobservable and non-contagion factors, Equation (4) and (5) reduces to Equation (2) and (3) respectively.

In principle, maximum likelihood estimates of the parameters can be obtained by jointly maximizing the likelihood function $$L(\zeta_j, \alpha_i^c, \alpha_i^{-c}) = \prod_j f(\zeta_j) \prod_i \prod_l \prod_t P_{ijlt}^{Y_{ijlt}} (1-P_{ijlt})^{1-Y_{ijlt}} \quad (6)$$

assuming conditional independence among the infection of disease or adoption of product across different occasions as well as individuals, which means that an individual's infection of disease or adoption of product after contacting to different potential infectious individuals across different occasions may be positively correlated but all this correlation can be entirely explained by the infectivity and susceptibility of the individuals and the correlation among environmental covariates.

We can see that presently the model is over parameterized and the Maximum Likelihood Estimation is not identifiable. One solution is to impose restrictions to the latent trait parameters, such as $\Sigma \alpha_i^c=1$ or to set specific distribution, for instance, $\zeta_j \sim N(0,1)$ and to focus on susceptibility parameters by integrating the parameters $\zeta_j$ out of the joint likelihood function.

Assuming $\epsilon_{ilt}$ to be Logistic distribution we can solve out the unknown susceptibility and sensitivity parameters from the below equations:

$$\sum_j^J \sum_l \sum_t Y_{ijlt} x_{jl(t-1)} n_{ijlt} \quad (7)$$

$$\int \zeta_j p(\zeta_j \mid Y_{ijlt}, \alpha_i^c, \alpha_i^{-c}, x_{jl(t-1)}, n_{ijlt}, X_{ilt}) d\zeta_j =$$

$$\sum_j^J \sum_l \sum_t x_{jl(t-1)} n_{ijlt}$$

$$\int \frac{\zeta_j \exp(\alpha_i^c \zeta_j x_{jl(t-1)} n_{ijlt} + X'_{ilt}\alpha_i^{-c}) p(\zeta_j \mid Y_{ijlt}, \alpha_i^c, \alpha_i^{-c}, x_{jl(t-1)}, n_{ijlt}, X_{ilt})}{1 + \exp(\alpha_i^c \zeta_j x_{jl(t-1)} n_{ijlt} + X'_{ilt}\alpha_i^{-c})} d\zeta_j$$

$$\sum_j^J \sum_l \sum_t Y_{ijlt} X_{ilt1} \int \zeta_j p(\zeta_j \mid Y_{ijlt}, \alpha_i^c, \alpha_i^{-c}, x_{jl(t-1)}, n_{ijlt}, X_{ilt}) d\zeta_j = \quad (8)$$

$$\sum_j^J \sum_l \sum_t X_{ilt1}$$

$$\int \frac{\exp(\eta_{ijlt}) p(\zeta_j \mid Y_{ijlt}, \alpha_i^c, \alpha_i^{-c}, x_{jl(t-1)}, n_{ijlt}, X_{ilt})}{1 + \exp(\alpha_i^c \zeta_j x_{jl(t-1)} n_{ijlt} + X'_{ilt}\alpha_i^{-c})} d\zeta_j$$

...

$$\sum_j^J \sum_l \sum_t Y_{ijlt} X_{iltk} \int \zeta_j p(\zeta_j \mid Y_{ijlt}, \alpha_i^c, \alpha_i^{-c}, x_{jl(t-1)}, n_{ijlt}, X_{ilt}) d\zeta_j = \quad (9)$$

$$\sum_j^J \sum_l \sum_t X_{iltk}$$

$$\int \frac{\exp(\eta_{ijlt}) p(\zeta_j \mid Y_{ijlt}, \alpha_i^c, \alpha_i^{-c}, x_{jl(t-1)}, n_{ijlt}, X_{ilt})}{1 + \exp(\alpha_i^c \zeta_j x_{jl(t-1)} n_{ijlt} + X'_{ilt}\alpha_i^{-c})} d\zeta_j$$

where $$p(\zeta_j \mid Y_{ijlt}, \alpha_i^c, \alpha_i^{-c}, x_{jl(t-1)}, n_{ijlt}, X_{ilt}) = \quad (10)$$

$$\frac{\Phi(\zeta_j) \prod_i \prod_l \prod_t P_{ijlt}^{Y_{ijlt}} (1-P_{ijlt})^{1-Y_{ijlt}}}{\int \Phi(\zeta_j) \prod_i \prod_l \prod_t P_{ijlt}^{Y_{ijlt}} (1-P_{ijlt})^{1-Y_{ijlt}} d\zeta_j}$$

Since this is computationally demanding and cannot be easily done using standard numerical methods, the present invention provides a Markov Chain Monte Carlo estimation which is based on the one proposed by Johnson and Albert (1999), but extends it to incorporate observable covariates and additional parameters in a setting of multilateral interactions among infectious and susceptible entities.

To implement the Gibbs sampler, a latent variable W is introduced so that $W_{ijlt} \geq 0$ if $Y_{ijlt}=1$ and $W_{ijlt}<0$ otherwise. Under the assumption of standard normal distributed error term, the joint posterior distribution of $(W, \alpha, \zeta)$ conditional on the observed data is $$p(\alpha, \zeta, W \mid \text{data}) \propto p(\text{data} \mid W) p(W \mid \alpha, \zeta) p(\alpha) p(\zeta). \quad (11)$$

Assume a normal prior for the individual parameter $\zeta_j \sim N(\nu, \sigma^2)$, which means that the individual entities' infectivity is normally distributed among the population. For the susceptibility and sensitivity parameter vector of the susceptible entity i, assume a conjugate multivariable normal prior $\alpha_i \sim N_k(\mu, \Sigma)$ and restrict the susceptibility parameter $\alpha_i^c$ to be positive which guarantees that entity i who interacts with a entity j with a positive (/negative) $\zeta_j$ should have a higher (/lower) probability to infect or adopt.

With prior distributions being specified, the fully conditional distributions of W, $\alpha$, and $\zeta$ for Bayesian estimation are given as below:

$$f(W_{ijlt} | *) \propto \text{Truncated } N(\alpha_i^c \zeta_j x_{jl(t-1)} n_{ijlt} + X'_{ilt} \alpha_i^{-c}, 1) \quad (12)$$

$$f(\zeta_j | *) \propto N\left(\left(D^T D + \frac{1}{\sigma^2}\right)^{-1}\left(D^T C + \frac{\nu}{\sigma^2}\right), \left(D^T D + \frac{1}{\sigma^2}\right)^{-1}\right) \quad (13)$$

$$f(\alpha_i | *) \propto N((F^T F + \Sigma^{-1})^{-1}(F^T E + \Sigma^{-1} \mu),$$
$$(F^T F + \Sigma^{-1})^{-1}) I(\alpha_i^c > 0) \quad (14)$$

where $$C = [W_{ijlt} - X'_{ilt} \alpha_i^{-c}] \quad (15)$$

$$D = [\alpha_i^c x_{il(t-1)} n_{ijlt}] \quad (16)$$

$$E = [W_{ijlt}] \quad (17)$$

$$F = [\zeta_j x_{ijl(t-1)} n_{ijt} X'_{ilt}] \quad (18)$$

To estimate the enhanced model (Equation 5), a new latent variable Z is included such that $$P(Z_{ijlt}=1 | Y_{ijlt}=1) = \Phi(\alpha_i^c \zeta_j x_{jl(t-1)} n_{ijlt} + X_{ilt}' \alpha_i^{-c});$$
$$(Z_{ijlt}=0 | Y_{ijlt}=1) = \beta_{il}(1 - \Phi(\alpha_i^c \zeta_j x_{jl(t-1)} n_{ijlt} +$$
$$X_{ilt}' \alpha_i^{-c})) \quad (19)$$

$$p(Z_{ijlt}=1 | Y_{ijlt}=0) = 0; \ p(Z_{ijlt}=0 | Y_{ijlt}=0) = 1 \quad (20)$$

And the joint posterior distribution of (Z, W, $\alpha$, $\zeta$, $\beta$) conditional on the observed data is $$p(\alpha,\zeta,\beta,W,Z | \text{data}) \propto p(\text{data} | Z,\beta) p(Z|W) p(W|\alpha,\zeta) p(\alpha) p(\beta) p(\zeta) \quad (21)$$

Assuming a conjugate Bata prior distribution $\beta_{il} \sim \text{Bata}(c_{il}, d_{il})$, the posterior conditional distributions of $\beta_{il}$ for Bayesian estimation is as below:

$$f(\beta_{il}|*) \propto \text{Bata}(c_{il} + \Sigma_{(t|Z_{ilt}=0)} Y_{ilt}, d_{il} + \Sigma_t I(Z_{ilt}=0) - \Sigma_{(t|Z_{ilt}=0)} Y_{ilt}) \quad (22)$$

Figure 2:
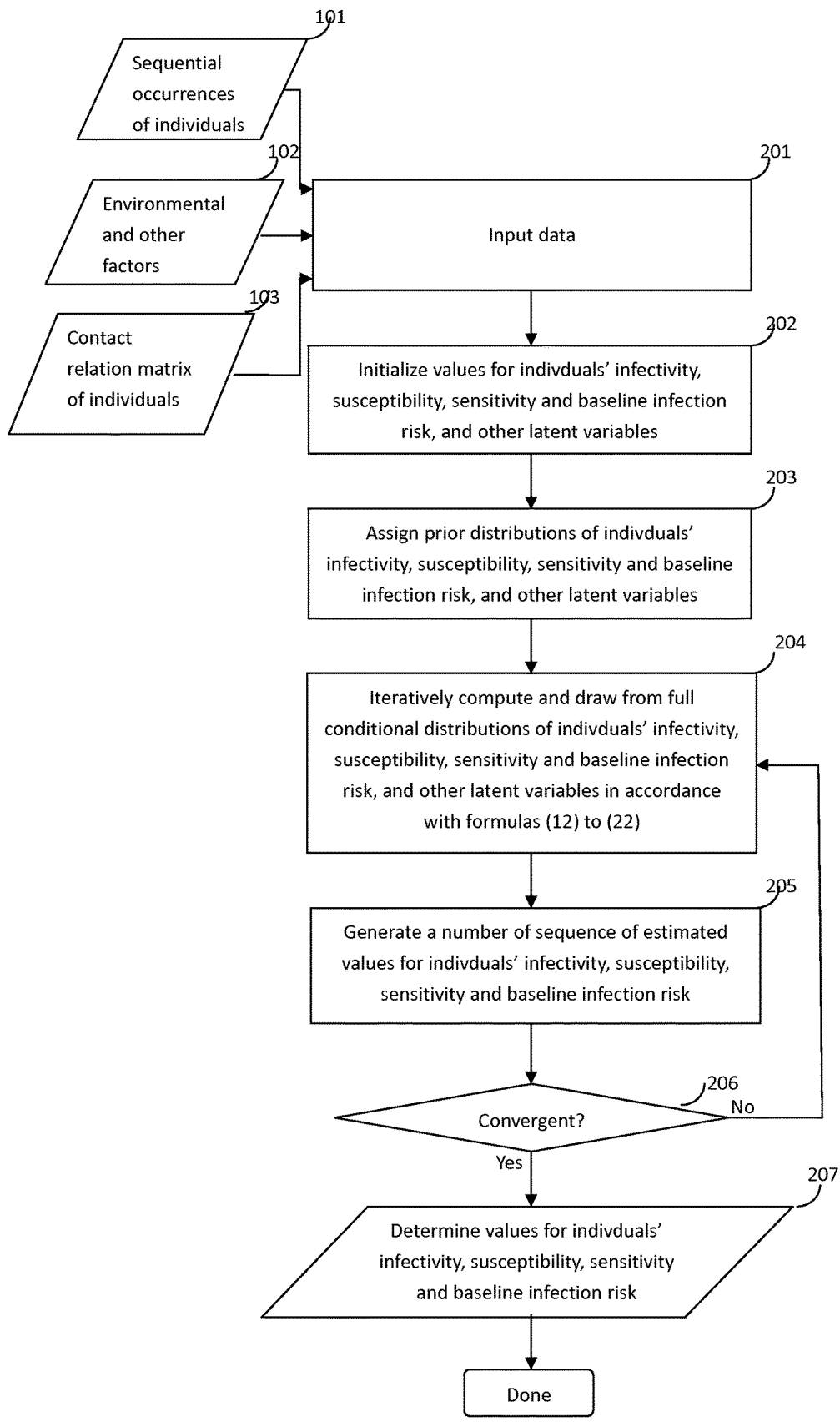
FIG. 2 is a flowchart of one embodiment of the invention.

FIG. 2 shows a flowchart of one embodiment of the present invention, which is a computer implemented Markov Chain Monte Carlo process for implementing the Bayesian estimation for all the parameters and latent variables. At step 101, the sequential occurrences, i.e., values of 0 or 1, of all the individual entities' disease infections or product adoptions are obtained as input data. At step 102, the conditions of all the environmental and other factors such as temperature, humidity and wind speed etc., or marketing mix such as price, promotion, as well as other disease (or product) related attributes confronted by the individual entities at various occasions are input. At step 103, the contact relation matrix between any two individuals that represent their explicit or implicit contact in different occasions are input. An element of the matrix can be 1 or 0 if the contact relation is accurate and explicit, or can be decimals and weighted value to reflect the likelihood of contact. The matrix can have more than two dimensions for multiple diseases, products or behaviors. At step 201, the obtained data is input into the storage devices for later use. At step 202, initial values for all the unknown parameters are set arbitrarily or randomly by computer. At step 203, the conjugate prior distributions are assumed and their hyperparameters are set arbitrarily, or by field experts. At step 204, the computer iteratively computes and draws from the full conditional distributions of individuals' infectivity, susceptibility, sensitivity and baseline infection risk, and other latent variables in accordance with formulas given by Equation (12) to Equation (22) stated in this specification. After an early burn-in period of iterations in step 204, Markov chains for each of the unknown parameters are generated and recorded by the computer in step 205. At step 206, the convergence of the chains are evaluated by comparison of the between and within variances for Markov chains or the R statistics suggested by Gelman and Rubin (2004). If the Markov chains converge, the values of each individual's infectivity, susceptibility, sensitivity and baseline infection risk parameters are determined at step 207. Otherwise, the computer return back to step 204, iteratively compute and draw more from the full conditional distributions.

Besides this embodiment of the present invention, a maximum likelihood estimation for susceptibility and sensitivity parameters based on Logistic distribution assumption can be obtained by solving Equations (7)-(10) stated in this specification, which demands more skills in numerical methods.

There are many ways that the present invention and its output can be used. For instance, the method can be used to rank and identify the most and least infectious and susceptible individuals for targeted vaccination, quarantine and in-depth genetic and pathological examinations. It can be used to identify key individual consumers for word-of-mouth marketing. It can also be used for identifying and monitoring problematic financial institutions or social riot sources. Moreover, there are many ways that this method can be adopted or altered for various purposes. As stated in the summary, this method provides an integrative latent trait framework that allows for various factors to be included into the model to play different roles. For example, more covariates, factors and latent traits can be added into the specifications, and altered forms of them can be used. Moreover, instead of using occurrences data, quantity data such as money can be examined, and different prior distributions and different link functions can be used. Further, the method can be used in various contexts wherein individual-level asymmetric dynamics occur, and for various types of entities among whom multilateral interactions and relation exist.

LIST OF REFERENCES

Watts and Dodds, "Influentials, Networks, and Public Opinion Formation," *Journal of Consumer Research*, 34(4), 441-458, 2007.

Goldenberg et al, "The Role of Hubs in the Adoption Processes," *Journal of Marketing*, 73, 1-13. 2009

Keeling and Rohani, *Modeling Infectious Diseases in Humans and Animals*. NJ, USA 2008.

Katz, "The two-step flow of communication: An Up-to-date Report on a Hypothesis," *Public Opinion Quart*, 21, 61-67 1957.

Weimann, "The Influentials: Back to the Concept of Opinion Leaders?" *Public Opinion Quarterly*, 55(2), 267-279, 1991.

Chaney, "Opinion Leaders as a Segment for Marketing Communications," *Marketing Intelligence and Planning*, 19(5), 302-308, 2001.

Thoburn, "Who are the Influencers," *Marketing*, 109 (29), 21, 2004.

Birnbaum, A., "Some latent trait models and their use in inferring an examinee's ability." In Lord, F. M. Novick, M. R. (Eds.), *Statistical theories of mental test scores*. Reading, Mass.: Addison-Wesley, 1968.

Freeman, "Centrality in Social Networks: Conceptual Clarification," *Social Networks*, 1, 215-239, 1979.

Case, "Spatial Patterns in Household Demand," *Econometrica*, 59 (4), 953-965, 1991.

Hambleton and Swaminathan, *Item response theory: Principles and applications*. Boston: Kluwer Academic Publishers, 1985.

Dodds and Watts, "A generalized model of social and biological contagion," *Journal of Theoretical Biology*, 232 (4), 587-604, 2005.

Rossi, Allenby and McCulloch, *Bayesian Statistics and Marketing*, Chichester: John Wiley & Sons Ltd, 2005.

Hartmann et al., "Modeling Social Interactions: Identification, Empirical Methods and Policy Implications," *Marketing Letters*, 19 (3), 287-304, 2008.

Trusov et al, "Determining Influential Users in Internet Social Networks", Journal of Marketing Research, 47(4), 2010.

Luo et al, "Identifying Infection Sources and Regions in Large Networks", *Signal Processing, IEEE Trans*, 61 (11), 2013.

Johnson and Albert, Ordinal Data Modeling, Springer, N.Y., 1999.

Gelman A et al., *Bayesian Data Analysis*. Chapman & Hall, Noca Raton, Fla., 2004.

The invention claimed is:

1. A computer implemented method for measuring infection traits of a plurality of individuals for a contagion, the method comprising:

receiving, contact information associated with contact between at least two individuals of the plurality of individuals, the contact information including at least one of a physical contact, a spatial proximity, a temporal proximity and a connection relationship;

generating, based on the received contact information, a contact relation matrix, the contact relation matrix includes matrix element values for each pair of individuals of the plurality of individuals, wherein the matrix element value is a 1 when contact between the pair of individuals is the physical contact, the matrix element value is a weighted decimal value when contact between the pair of individuals is at least one of the spatial proximity, the temporal proximity, and the connection relationship, and the matrix element value is a 0 when there is no contact between the pair of individuals, the contact relation matrix being updated as new contact information is received;

receiving, infection occurrence data for the contagion during an observation period for each of the plurality of individuals, the infection occurrence data including an infection status and a corresponding time of infection for each of the plurality of individuals;

generating a sequenced list of infection occurrence in the plurality of individuals based on the infection occurrence data, the sequenced list being updated in as new infection occurrence data is received;

receiving, environmental data associated with each of the plurality of individuals during the observational period;

generating a set of parameter estimations for each individual of the plurality of individuals based on the contact relation matrix, the sequenced list of infection occurrence, and the environmental data, the set of parameter estimation being iteratively generated based on the updating of the contact relation matrix, the sequenced list of infection occurrence, and the environmental data;

measuring infection traits for each individual of the plurality of individuals for a contagion based on the set of parameter estimations using an integrated latent trait response model, wherein the integrated latent trait response model changes in real time based on when the set of parameter estimations are iteratively generated;

ranking, in real-time, each individual of the plurality of individuals based on their measured infection traits for the contagion, wherein the rank of at least one of the plurality of individuals changes when the integrated latent trait response model changes;

based on the order of the ranked individuals, selecting at least one individual of the plurality of individuals, for further analysis; and generating a response plan based on additional information received from the at least one selected individual.

2. The method of claim 1, wherein the set of parameter estimations are Bayesian estimations iteratively generated using a Markov Chain Monte Carlo process.

3. The method of claim 2, wherein the Markov Chain Monte Carlo process further comprises:

obtaining for each individual of the plurality of individuals (i) the contact relation matrix N, (ii) the sequence list of infection occurrences Y, and (iii) the environmental data X;

initializing values for each individual of the plurality of individuals (i) an infectivity $\zeta$ and a susceptibility $\alpha^c$, (ii) a baseline infection risk or a baseline adoption likelihood $\beta$ to single or multiple diseases, (iii) a sensitivity $\alpha^{-c}$ to environmental factors, and (iv) latent variables Z and W for Gibbs sampling;

assigning, prior distributions of the infectivity, the susceptibility, the sensitivity to the environmental factors and the baseline infection risk or the baseline adoption likelihood of each of the individuals, in accordance with:

$\zeta \sim N(\nu, \sigma^2)$, $\alpha \sim N_k(\mu, \Sigma)$, $\beta \sim \text{Bata}(c, d)$, iteratively computing and sampling the infectivity, the susceptibility, the sensitivity of the environmental factors and the baseline infection risk or the baseline adoption likelihood, and the latent variables from a full conditional distribution in accordance with:

$$f(Z_{ijlt} \mid *) \propto B\left(\frac{\Phi(\alpha_i^c \zeta_j x_{jl(t-1)} n_{ijlt} + X'_{ilt} \alpha_i^{-c})}{\Phi(\alpha_i^c \zeta_j x_{jl(t-1)} n_{ijlt} + X'_{ilt} \alpha_i^{-c}) + \beta_{il}(1 - \Phi(\alpha_i^c \zeta_j x_{jl(t-1)} n_{ijlt} + X'_{ilt} \alpha_i^{-c}))}\right), \text{ for } Y_{ijlt} = 1$$

$$Z_{ijlt} = 0, \text{ for } Y_{ijlt} = 0$$

-continued $$f(W_{ijlt} | *) \propto \text{Truncated } N(\alpha_i^c \zeta_j x_{jl(t-1)} n_{ijt} + X'_{ilt} \alpha_i^{-c});$$

$$f(\zeta_j | *) \propto N\left(\left(D^T D + \frac{1}{\sigma^2}\right)^{-1}\left(D^T C + \frac{\nu}{\sigma^2}\right), \left(D^T D + \frac{1}{\sigma^2}\right)^{-1}\right)$$

$$f(\alpha_i | *) \propto N((F^T F + \Sigma^{-1})^{-1}(F^T E + \Sigma^{-1}\mu), (F^T F + \Sigma^{-1})^{-1})I(\alpha_i^c > 0)$$

$$C = [W_{ijlt} - X'_{ilt}\alpha_i^{-c}],$$

$$D = [\alpha_i^c x_{il(t-1)} n_{ijt}],$$

$$E = [W_{ijlt}],$$

$$F = [\zeta_j x_{ijl(t-1)} n_{ijt} X'_{ilt}]$$

$$f(\beta_{il} | *) \propto \text{Bata}\left(c_{il} + \sum_{(t|Z_{ilt}=0)} Y_{ilt}, d_{il} + \sum_t I(Z_{ilt}=0) - \sum_{(t|Z_{ilt}=0)} Y_{ilt}\right)$$

storing sequences of sampled estimates for the infectivity, the susceptibility, the sensitivity and the baseline infection risk for each of the individuals;

comparing a first sequence of the sampled estimate and a second sequence sampled estimate of the stored sequence of sampled estimates for each of the individuals calculating convergence statistics for each individual;

updating and determining the estimates of each individual entity's infectivity, susceptibility, sensitivity and baseline infection risk until convergence.

4. The method of claim 2, wherein the likelihood maximization process further comprises:

obtaining for each individual of the plurality of individuals (i) the contact relation matrix N, (ii) the sequence list of infection occurrences Y, and (iii) the environmental data X;

calculating a joint likelihood function for an infectivity $\zeta$, a susceptibility $\alpha^c$, and a sensitivity $\alpha^{-c}$ based on the obtained data for each individual of the plurality of individuals, in accordance with:

$$L(\zeta_j, \alpha_i^c, \alpha_i^{-c}) = \prod_j f(\zeta_j) \prod_i \prod_l \prod_t P_{ijlt}^{Y_{ijlt}} (1 - P_{ijlt})^{1-Y_{ijlt}}$$

maximizing the joint likelihood function by imposing restrictions on each of the individuals infectivity, wherein the infectivity is $\Sigma\alpha^c=1$ and susceptibility is $\zeta \sim N(0, 1)$; and determining, for each of the individuals, the susceptibility and the sensitivity based on a set of equations, the set of equations including:

$$\sum_j^J \sum_l \sum_t Y_{ijlt} x_{jl(t-1)} n_{ijt} \int \zeta_j p(\zeta_j | Y_{ijlt}, \alpha_i^c, \alpha_i^{-c}, x_{jl(t-1)}, n_{ijt}, X_{ilt}) d\zeta_j =$$

$$\sum_j^J \sum_l \sum_t x_{jl(t-1)} n_{ijt} \int \frac{\zeta_j \exp(\alpha_i^c \zeta_j x_{jl(t-1)} n_{ijt} + X'_{ilt}\alpha_i^{-c})}{1 + \exp(\alpha_i^c \zeta_j x_{jl(t-1)} n_{ijt} + X'_{ilt}\alpha_i^{-c})} p(\zeta_j | Y_{ijlt}, \alpha_i^c, \alpha_i^{-c}, x_{jl(t-1)}, n_{ijt}, X_{ilt}) d\zeta_j$$

$$\sum_j^J \sum_l \sum_t Y_{ijlt} X_{ijlt} \int \zeta_j p(\zeta_j | Y_{ijlt}, \alpha_i^c, \alpha_i^{-c}, x_{jl(t-1)}, n_{ijt}, X_{ilt})$$

$$d\zeta_j = \sum_j^J \sum_l \sum_t X_{iltl}$$

-continued $$\int \frac{p(\zeta_j | Y_{ijlt}, \alpha_i^c, \alpha_i^{-c}, x_{jl(t-1)}, n_{ijt}, X_{ilt}) \exp(\alpha_i^c \zeta_j x_{ij(t-1)} n_{ijt} + X'_{ilt}\alpha_i^{-c})}{1 + \exp(\alpha_i^c \zeta_j x_{jl(t-1)} n_{ijt} + X'_{ilt}\alpha_i^{-c})} d\zeta_j$$

...

$$\sum_j^J \sum_l \sum_t Y_{ijlt} X_{iltk} \int \zeta_j p(\zeta_j | Y_{ijlt}, \alpha_i^c, \alpha_i^{-c}, x_{jl(t-1)}, n_{ijt}, X_{ilt}) d\zeta_j =$$

$$\sum_j^J \sum_l \sum_t X_{iltk}$$

$$\int \frac{p(\zeta_j | Y_{ijlt}, \alpha_i^c, \alpha_i^{-c}, x_{jl(t-1)}, n_{ijt}, X_{ilt}) \exp(\alpha_i^c \zeta_j x_{jl(t-1)} n_{ijt} + X'_{ilt}\alpha_i^{-c})}{1 + \exp(\alpha_i^c \zeta_j x_{jl(t-1)} n_{ijt} + X'_{ilt}\alpha_i^{-c})} d\zeta_j$$

where $$p\left(\begin{array}{c}\zeta_j | Y_{ijlt}, \alpha_i^c, \alpha_i^{-c}, \\ x_{jl(t-1)}, n_{ijt}, X_{ilt}\end{array}\right) = \frac{\Phi(\zeta_j) \prod_i \prod_l \prod_t P_{ijlt}^{Y_{ijlt}}(1-P_{ijlt})^{1-Y_{ijlt}}}{\int \Phi(\zeta_j) \prod_i \prod_l \prod_t P_{ijlt}^{Y_{ijlt}}(1-P_{ijlt})^{1-Y_{ijlt}} d\zeta_j}.$$

5. The method of claim 1, wherein the integrated latent trait response model represents a conditional infection probability of each of the plurality of individuals using at least one of a normal distribution, a logistic distribution and a probability distribution.

6. The method of claim 1, wherein the set of parameter estimations are Bayesian estimations iteratively generated using a likelihood maximization process.

7. The method of claim 1, wherein measuring the infectivity of the contagion for each individual of the plurality of individuals includes relating a conditional infection probability of a susceptible individual with at least one index deduced from the sequenced list of infection occurrence of each of the individuals or of a group of selected individuals.

8. The method of claim 1, wherein measuring infection traits for each individual of the plurality of individuals for the contagion further includes:

analyzing a plurality of sequential contagion events amongst the plurality of individuals;

estimating the latent trait response model, the latent trait response model being based at least in part on (i) an infectivity and an infection status of a potential infectious individual, (ii) a susceptibility of a potential susceptible individual, (iii) the contact relation matrix, (iv) the environmental data, and (vi) a baseline infection risk of the potential susceptible individual; and providing, to at least one of the individuals of the plurality of individuals, the infectivity, the susceptibility, the sensitivity and the baseline infection risk measurements for the contagions.

9. The method of claim 1, wherein the plurality of individuals individual include at least one of: humans, animals, plants, organizations, particles, and machines.

10. The method of claim 1, wherein the contagions are at least one of a biological contagion and a social contagion, and the contagions include at least one of: infectious diseases, fashions, product adoptions, service adoptions, financial shocks, riots, behaviors, and opinions.

11. The method of claim 1, wherein the environmental data includes at least one of: temperature, humidity, wind speed, living conditions, product attributes, price, promotion, channel, entity characteristics, and market characteristics.

12. The method of claim 1, further comprising:
selecting at least one individual of the plurality of individuals, that may need quarantining; and
determining whether to quarantine the at least one individual.

13. The method of claim 1, further comprising:
based on the ranking order of a susceptibility risk and a baseline infection risk, selecting at least one individual of the plurality of individuals for genetic examinations or behavioral analysis, wherein the at least one susceptibility risk and the baseline infection risk is the infection trait.

14. The method of claim 1, further comprising:
based on the measured infection trait, adjusting environmental factors for at least one individual of the plurality of individuals, wherein the infection trait is a sensitivity to environmental factors.

15. The method of claim 1, wherein the integrated latent trait response model enables joint inferences of heterogeneous measurements for each of the plurality of individuals based on at least the contact relation matrix, the sequence list of infection occurrences, and environmental data.

16. A system for measuring infection traits of a plurality of individuals for a contagion, the system comprising:
a processor; and
one or more stored sequences of instructions which, when executed by the processor, cause the processor to:
receive, contact information associated with contact between at least two individuals of the plurality of individuals, the contact information including at least one of a physical contact, a spatial proximity, a temporal proximity and a connection relationship;
generate, based on the received contact information, a contact relation matrix, the contact relation matrix includes matrix element values for each pair of individuals of the plurality of individuals, wherein the matrix element value is a 1 when contact between the pair of individuals is the physical contact, the matrix element value is a weighted decimal value when contact between the pair of individuals is at least one of the spatial proximity, the temporal proximity, and the connection relationship, and the matrix element value is a 0 when there is no contact between the pair of individuals, the contact relation matrix being updated as new contact information is received;
receive, infection occurrence data for the contagion during an observation period for each of the plurality of individuals, the infection occurrence data including an infection status and a corresponding time of infection for each of the plurality of individuals;
generate a sequenced list of infection occurrence in the plurality of individuals based on the infection occurrence data, the sequenced list being updated in as new infection occurrence data is received;
receive, environmental data associated with each of the plurality of individuals during the observational period;
generate a set of parameter estimations for each individual of the plurality of individuals based on the contact relation matrix, the sequenced list of infection occurrence, and the environmental data, the set of parameter estimation being iteratively generated based on the updating of the contact relation matrix, the sequenced list of infection occurrence, and the environmental data;
measure infection traits for each individual of the plurality of individuals for a contagion based on the set of parameter estimations using an integrated latent trait response model, wherein the integrated latent trait response model changes in real time based on when the set of parameter estimations are iteratively generated;
rank, in real-time, each individual of the plurality of individuals based on their measured infection traits for the contagion, wherein the rank of at least one of the plurality of individuals changes when the integrated latent trait response model changes;
transmitting the rank and the measured infection trait for the contagion for at least one of the plurality of individuals, wherein transmitting includes at least one of describing, displaying and communicating the rank and the measured infection trait;
based on the order of the ranked individuals, select at least one individual of the plurality of individuals, for further analysis; and
generate a response plan based on additional information received from the at least one selected individual.

17. The system of claim 16, wherein the set of parameter estimations are Bayesian estimations iteratively generated using a Markov Chain Monte Carlo process.

18. The system of claim 16, wherein measuring the infectivity of the contagion for each individual of the plurality of individuals is further based on relating a conditional infection probability of a susceptible individual with at least one index deduced from the sequenced list of infection occurrence of each individual entity.

19. The system of claim 16, wherein one or more steps are performed randomly, at certain frequency or at a real-time basis.

20. The system of claim 16, wherein the contact information, infection occurrence data, and the environmental data is received from multiple channels including at least one of sensors, cameras recorders, databases, searching information and crawling web.

21. The system of claim 16, wherein,
the integrated latent trait response model enables joint inferences of heterogeneous measurements for each of the plurality of individuals based on at least the contact relation matrix, the sequence list of infection occurrences, and environmental data.

* * * * *